United States Patent [19]
Mirzabekov et al.

[11] Patent Number: 5,861,247
[45] Date of Patent: Jan. 19, 1999

[54] RAPID METHOD TO DETECT DUPLEX FORMATION IN SEQUENCING BY HYBRIDIZATION METHODS

[75] Inventors: Andrei Darievich Mirzabekov; Edward Nikolaevich Timofeev; Vladimer Leonidovich Florentiev; Eugene Vladislavovich Kirillov, all of Moscow, Russian Federation

[73] Assignee: University of Chicago

[21] Appl. No.: 592,120

[22] Filed: Jan. 26, 1996

[51] Int. Cl.⁶ ............................................... C12Q 1/68
[52] U.S. Cl. ................................ 435/6; 935/77; 935/78
[58] Field of Search ................. 435/6, 91.2; 536/22.1, 536/24.3, 24.33; 436/800, 807, 809, 527, 528; 427/2.11

[56] References Cited

U.S. PATENT DOCUMENTS

| | | | |
|---|---|---|---|
| 5,552,270 | 9/1996 | Khrapko et al. | 435/6 |
| 5,582,984 | 12/1996 | Bieniarz et al. | 435/6 |

FOREIGN PATENT DOCUMENTS

| | | | |
|---|---|---|---|
| WO 95/08642 | 3/1995 | WIPO | C12Q 1/68 |

OTHER PUBLICATIONS

Southern, et al., Analyzing and Comparing Nucleic Acid Sequences by Hybridization to Arrays of Oligonucleotides: Evaluation Using Experimental Models, Genomics 13:1008–1017, 1992.

*Primary Examiner*—Lisa B. Arthur
*Attorney, Agent, or Firm*—Cherskov & Flaynik

[57] ABSTRACT

A method for determining the existence of duplexes of oligonucleotide complementary molecules is provided whereby a plurality of immobilized oligonucleotide molecules, each of a specific length and each having a specific base sequence, is contacted with complementary, single stranded oligonucleotide molecules to form a duplex so as to facilitate intercalation of a fluorescent dye between the base planes of the duplex. The invention also provides for a method for constructing oligonucleotide matrices comprising confining light sensitive fluid to a surface, exposing said light-sensitive fluid to a light pattern so as to cause the fluid exposed to the light to coalesce into discrete units and adhere to the surface; and contacting each of the units with a set of different oligonucleotide molecules so as to allow the molecules to disperse into the units.

10 Claims, 7 Drawing Sheets

CCTGGGCAGGTTGGTATCA
matrix-CyAACCxT-5'

RAPID METHOD TO DETECT DUPLEX FORMATION IN SEQUENCING BY HYBRIDIZATION METHODS

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to a method for rapidly detecting the presence of duplex formation between single stranded nucleotide macromolecules, and more specifically, this invention relates to a method for using oligonucleotide arrays to rapidly detect duplex formation of oligonucleotide sequences. This invention also relates to a simple procedure for producing the oligonucleotide-arrays.

2. Background of the Invention

Present techniques for determining the existence of target sequences in patient DNA are complex, inefficient and somewhat time consuming. For example, one multi-step DNA sequencing approach, the Maxam and Gilbert method, involves first labeling DNA, and then splitting the DNA with a chemical, designed to alter a specific base, to produce a set of labeled fragments. The process is repeated by cleaving additional DNA with other chemicals specific for altering different bases, to produce additional sets of labeled fragments. The multiple fragment sets then must be run side-by-side in electrophoresis gels to determine base sequences.

Another sequencing method, the dideoxy procedure, based on Sanger, et al. *Proc. Natl. Acad. Sci. USA* 74, 5463–7 (1977) first requires the combination of a chain terminator as a limiting reagent, and then the use of polymerase to generate various length molecules, said molecules later to be compared on a gel. The accompanying lengthy electrophoresis procedures further detracts from the utility of this method as a fast and efficient sequencing tool.

A more recently developed sequencing strategy involves sequencing by hybridization on oligonucleotide microchips, or matrices, (SHOM) whereby DNA is hybridized with a complete set of oligonucleotides, which are first immobilized at fixed positions on a glass plate or polyacrylamide gel matrix. There are drawbacks to this technique, however. For instance, given that short nucleotide sequences are repeated rather frequently in long DNA molecules, the sequencing of lengthy genome strings is not feasible via SHOM. Also, hybridization with short oligonucleotides is affected by hairpin structures in DNA.

Furthermore, SHOM requires the utilization of high volume substrates containing many thousands of cells. If immobilized octamers are utilized to determine the positions of each of the four bases in genomic DNA, for example, then $4^8$ or 65,536 such octamers, themselves which would need to be previously fabricated, would have to be immobilized in individual cells on the gel matrix.

The production of literally thousands of these cells on the polyacrylamide substrates is problematic. First, these cells must be accurately spaced relative to one another. Second, these cells must be of sufficient depth and volume to hold predetermined amounts of the oligonucleotide. Cell sizes can range from 25 microns ($\mu$m) to 1000 $\mu$m.

Typically, cells are produced in a myriad of ways. Two-dimensional scribing techniques and laser evaporation are two typical methods of cell formation. Mechanical scribing techniques are limited, however, in that the smallest structures which can be produced via this method are approximately 100 $\mu$m×100 $\mu$m. Lasers applications, because of their expense, also are limiting. Furthermore, both of these procedures require complex equipment and experienced personnel.

A need exists in the art to provide a rapid and efficient method for detecting the existence of complementary sequences to target DNA strands. This detection method should be performed using standard reagents found in a typical biochemistry facility. A need also exists for a method to produce accurate polyacrylamide matrices to be used in the above-disclosed duplex detection method. Such a matrix production method also must be simple enough to be performed in typically-equipped biochemical laboratories.

SUMMARY OF THE INVENTION

It is an object of the present invention to provide a method for rapidly detecting the formation and existence of duplexes between complementary nucleotide sequence strands that overcomes many of the disadvantages and reliability shortcomings of the prior art.

Another object of the present invention is to provide a method for the detection of DNA duplexes. A feature of the invention is the use of intercalating dyes. An advantage of the invention is the rapid detection of duplexes using typically-outfitted laboratories to perform standard procedures with common reagents.

Yet another object of the present invention is to provide a highly efficient method for detecting DNA duplexes. A feature of the invention is contacting a DNA duplex, contained on a high-volume support substrate, with an intercalating agent. An advantage of the invention is the enhanced ability to detect small amounts of formed DNA duplexes using standard, low-cost laboratory reagents.

Still another object of the present invention is to provide a method for producing a polyacrylamide matrix having thousands of individual and well defined holding cells. A feature of the invention is the use of mask-controlled photopolymerization processes. An advantage of the invention is the rendering of high numbers of precise cell geometries and at high densities.

Briefly, the invention provides for a method for determining the existence of duplexes of oligonucleotide complementary molecules comprising constructing a plurality of different oligonucleotide molecules each of a specific length and each having a specific base sequence; supplying a matrix having a plurality of cells adapted to receive and immobilize the oligonucleotide molecules; immobilizing the different oligonucleotide molecules in the cells to fill the cells; contacting the now-filled cells with single stranded oligonucleotide molecules to form a duplex; contacting the duplex with an intercalating agent; and observing fluorescence levels emanating from the now-contacted duplex. A first fluorescence level is observed after the oligonucleotide molecules are immobilized to the matrix. The specific length of the different oligonucleotide molecules is selected from a range of between approximately 5 nucleotides and 30 nucleotides.

The invention also provides for a method for constructing oligonucleotide matrices comprising confining light sensitive fluid to a surface, exposing said light-sensitive fluid to a light pattern so as to cause the fluid exposed to the light to coalesce into discrete units and stick to the surface; and contacting each of the units with a set of different oligonucleotide molecules so as to allow the molecules to disperse into the units.

BRIEF DESCRIPTION OF THE DRAWING

The invention together with the above and other objects and advantages will be best understood from the following detailed description of the preferred embodiment of the invention shown in the accompanying drawing, wherein.

DETAILED DESCRIPTION OF THE INVENTION

This invention involves incorporating intercalating techniques with processes for sequencing genetic material by hybridization methods (SBH) so as to produce a simple low resolution procedure for duplex formation analysis. This invention also teaches a method to produce polyacrylamide matrices having thousands of microscopic-sized, precisely configured and positioned holding cells designed to contain predetermined quantities of oligonucleotide mixtures.

The inventors have developed a method of using a mask-controlled photo-polymerization process to create micro-matrix topologies. The resulting micro-matrices are used to immobilize specific oligonucleotide strands designed to form duplexes with target DNA. The duplexes are contacted with an intercalating substance or dye to alert clinicians to the presence of duplexes.

Array Manufacturing Detail

The array manufacturing method, noted supra, incorporates a modified Methylene Blue induced photo-polymerization procedure whereby a polyacrylamide solution is prepared and then configured into desired shapes and sizes for subsequent polymerization.

Figure 1:
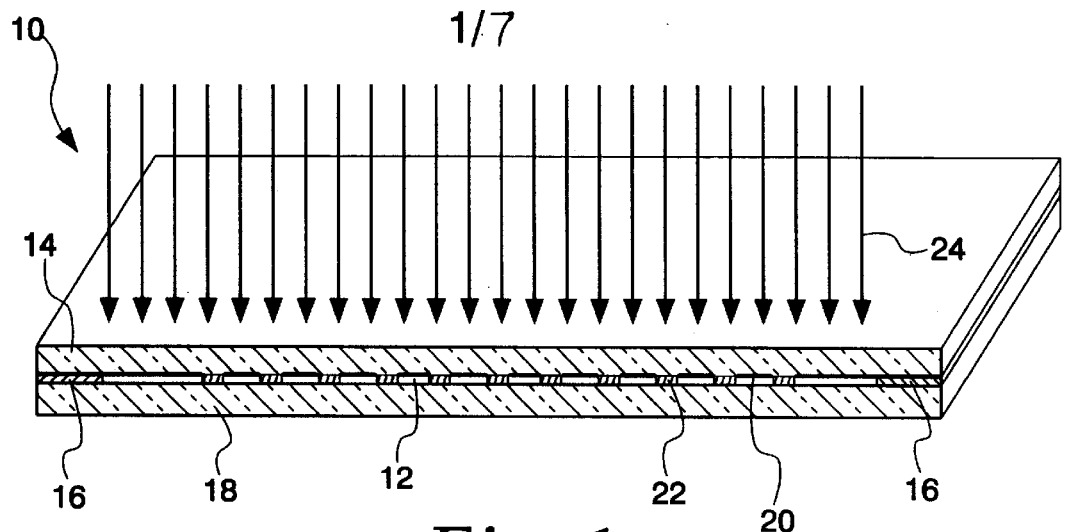
FIG. 1 is an elevated view of an polyacrylamide matrix assembly, in accordance with the present invention.
Figure 2:
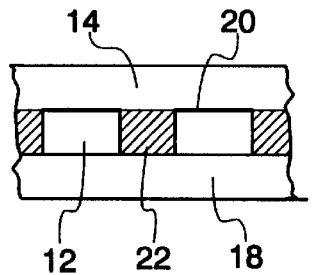
FIG. 2 is a magnified view of the polyacrylamide matrix assembly illustrated in FIG. 1, in accordance with the present invention.

The production of gel-matrices involves the construction of polymerization units into which prepared acrylamide fluids are placed. One exemplary polymerization unit is depicted in FIG. 1, as numeral 10, and partially magnified in FIG. 2.

In one embodiment of the invention, photo-polymerizations are performed on a solution containing 40 percent (between 30–45 percent, is suitable) acrylamide/Methylene Bis-Acrylamide (30:1) stock solution and 0.04 percent Methylene blue stock solution in water. The stock acrylamide solution is diluted with water to a concentration ranging from 4 to 8 percent and subsequently degassed with a water pump for 10 minutes. The gel matrix is prepared from a standard mixture of 0.5 μl 0.04 percent Methylene blue solution, 1 ml acrylamide solution and 10 μl N,N,N', N'-tetramethylethilendiamine (TEMED), from Aldrich (Milwaukee, Wis.).

The resulting, liquid (prepolymerized) mixture 12 is applied to a first surface of a quartz substrate 14, which is previously manipulated to contain a photomask. The preparation of the quartz substrate 14 involves applying a mask 20 to the first surface of the substrate 14, and then pretreating the first surface with an anti-wetting agent or an agent to increase the hydrophobicity of the surface. One such anti-wetting agent is a 2 percent solution of dimethyldichlorosilane in 1,1,1,-trichloroethane, having the trade name Repel-Silan™, and manufactured by Pharmacia Biotech of Uppsala, Sweden. Another suitable anti-wetting agent is trimethylchlorsilane. Two identical spacers 16, made from an inert material such as Teflon, of 20 μm thickness are placed on peripheral edges of the first surface of the quartz substrate so as form a pan-like container to confine the mixture 12. As such, a myriad of spacer thicknesses can be employed, depending on the final desired thickness of the polynucleotide chip.

A glass microscope slide 18, first pretreated with a material to attach polyacrylamide to glass, is placed on top of the spacers 16 to form a glass chamber 10. An exemplary pretreatment material is γ-Methacryloxy-propyl-trimethoxysilane, manufactured as Bind Silane by Pharmacia. This entire assembly or chamber 10 is fastened together via a myriad of fastening means (not shown), such as paper clips, tape, or inert adhesive.

A first surface of the quartz substrate 14 has a nontransparent mask (e.g., comprised of an inert opaque material such as chrome coating or permanent ink), containing a (grid) 20 defining a pattern of the desired topology. The grid 20 is applied to the mask coating surface of the quartz substrate 14 either by hand with a fine point marker or by photolithography, with the size of the gel elements defined by the dimensions of the transparent squares etched into the mask.

Figure 3:
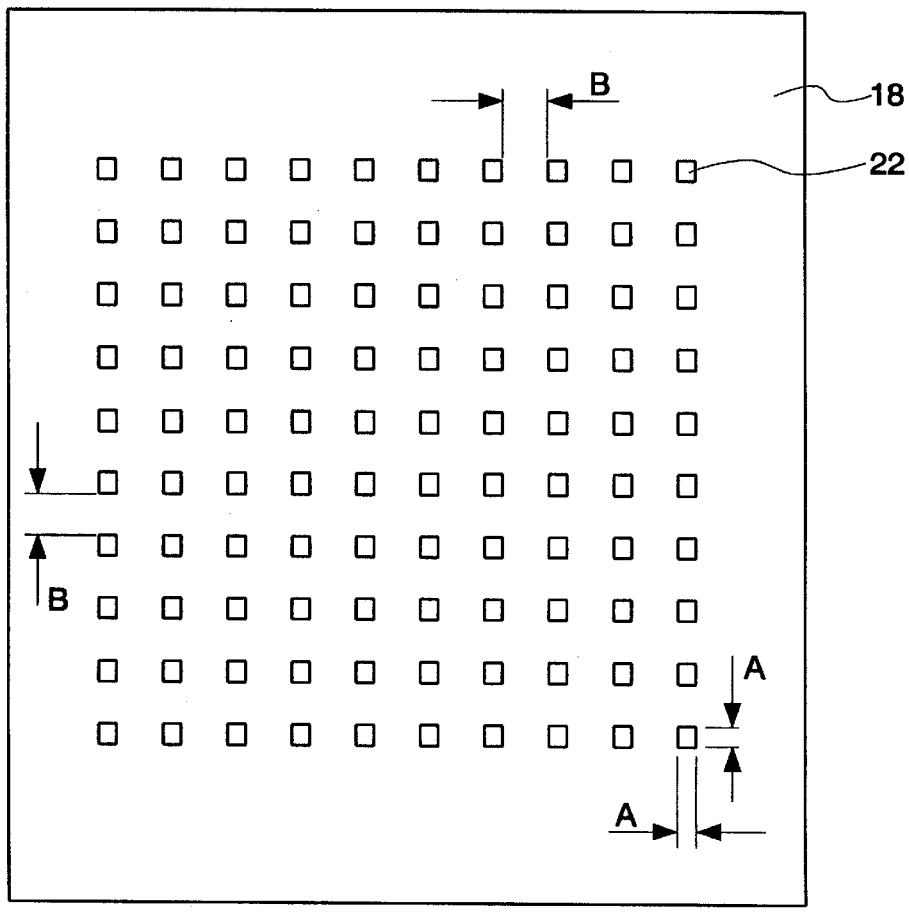
FIG. 3 is a plan view of a gel matrix, manufactured in accordance with the present invention.

An exemplary grid is depicted in FIG. 3. Dimensions labeled as element "A" are the sizes of gel cells while elements "B" are illustrated as the spaces between the cells. The mask is designed to block the light, used in the light-induced acrylamide polymerization process, in the spaces "B" between the gel units 22 where gel coalescence is not desired.

Various sizes of gel cells were fabricated on separate masks, as disclosed in Table 1, below.

TABLE 1

Various Gel and Space Dimensions Obtained Via the
Invented Process of Light-Induced Polyacrylamide Polymerization.

| Mask # | Dimensions ($\mu$m) | |
| --- | --- | --- |
| | Gel Cells | Interstitial Spaces |
| 1 | 25 | 50 |
| 2 | 40 | 80 |
| 3 | 100 | 200 |
| 4 | 500 | 1,000 |
| 5 | 1,000 | 2,000 |

After assembly, the assembled polymerization unit 10 is placed under a light source, such as a 312 nm UV-transilluminator such that the quartz substrate is closest to the source. Good results are obtained when the actual photomask layer 20, first deposited on the first surface of the quartz substrate 14, is in contact with the acrylamide solution. UV exposures of approximately 20 minutes provide good results. A myriad of wavelengths are suitable for the light-induced polymerization process, including those found in the range of between approximately 250 nm and 320 nm.

After exposure, the chamber 10 is disassembled. To facilitate disassembly, the chamber 10 can be placed in a water bath at room temperature. As noted supra, gel matrix units 22 are retained on the glass where light is allowed to permeate through the mask. These units 22 are separated from each other as a result of opaque mask portions, between the unit regions, precluding gel polymerization.

The resulting gel matrix is washed with water, placed in a solution for a period of time to introduce primary amino groups into the acrylamide (an exemplary solution being hydrazine hydrate). This period of time can range from 35–45 minutes. The matrix is then washed with water, and then treated to neutralize the remnants of the basic pH hydrazine treatment. One such neutralization procedure is placing the matrix in 1 percent acetic acid until neutralization is achieved, perhaps for 10 minutes. After neutralization, the matrix is washed with water, and then treated to remove any electrostatically sorbed chemicals. One such treatment involves placing the matrix in 1M NaCl for approximately 10 minutes. After a final washing with water, the unit is left to dry, and then treated with a thin film of an anti-wetting agent, such as Repel-Silan so as to make the interstitial glass spaces, designated as "B" in FIG. 3, hydrophobic. This will further isolate the gel units 22 from each other to minimize cross contamination during oligonucleotide loading. Treatment of the anti-wetting agent is brief, approximately 1 minute. The matrix is rendered ready for oligonucleotide loading after a final washing with ethanol (from 96 percent to neat) and then water to remove the ethanol.

Oligonucleotide Loading Detail

The inventors have developed a specific method for loading oligonucleotides onto matrices which are produced via the method outlined above. The method is fully disclosed in PCT/RU94/00179, filed on Aug. 11, 1993 to Mirzabekov. Described briefly, a pin is immersed into, and is wetted with, oligonucleotide solution. After being withdrawn from the solution, the pin is contacted with the gel surface.

During oligonucleotide aspiration, transfer and deposition, the temperature of the pin must be maintained near dew point at ambient temperature so as to prevent evaporation. Otherwise, the viscosity of the solution microvolumes (typically 10 nanoliters or less) will lead either to complete evaporation or to incomplete transfer of the desired dose.

The invented transfer method allows for the transfer of a range of micro-volumes of oligonucleotide solutions, from 0.3 to 50 nanoliters (nl), with a dispensing error of no more than approximately ±20 percent. As disclosed in the above-identified PCT application PCT/RU94/00179, the device for microdispensing aqueous solutions of solutions is depicted in FIGS. 6–10. The device comprises a base 1 shaped as a rectangular plate, one side of which carries a plurality of rods 2 held with one of their ends to said plate. The rods 2 are arranged parallel to one another and spaced equidistantly to one another. Butt ends 3 of the rods are coplanar with one another and parallel to the base 1. A battery 4 of thermoelectric cells (e.g. Peltier elements) adjoins the base 1 on the side opposite to that equipped with the rods 2 and is in heat contact therewith. In this particular embodiment, the battery 4 is shaped similar in size to the base 1. The battery 4 is connected through wires, 5, to a controlled source 6 of direct-current. The battery 4 of thermoelectric cells is a means for maintaining the temperature of the butt ends 3 of the rods 2 equal essentially to the dew point of the ambient air. With its other side, the battery 4 of Peltier elements adjoins the surface of a flow-block radiator 7 and is in heat contact therewith. To provide a uniform heat contact between the surface of the battery and the base on one side, and between the radiator 7 on the other side, provision is made for thin (under 100 microns thick) layers 8 of a heat-conductive paste based on beryllium oxide and polydimethylsiloxane oil.

The base 1 and the rods 2 are made from a material having high thermal conductivity, preferably from a metal, such as copper or brass. The radiator 7 can be a silicon slab.

The rods 2 are provided with a heat-insulating coating 9 applied to half their length, including from the point of the rod attachment to the base plate 1. Material for the coating in this region can be polyolefin. One polyolefin product is Heat Shrinkable Pack, available through RS Components Ltd., England. The heat insulating coating 9 used to protect the surface of the base 1 exposed to atmospheric air can be formed polyurethane.

The rods 2 in the embodiment illustrated are round in cross-section (though they may have any other cross-sectional shape) and their vacant ends are shaped as cone frustums tapering to the ends. A hydrophilic coating 30 such as glass or gold, is applied to the butt ends 3 of the rods 2, whereas a hydrophobic coating 11 such as fluoroplastic, or glass whose surface is hydrophobized by treatment with Repel Silane, is applied to the side surfaces of the vacant ends of the rods.

The area of the butt ends 3 of the rods is selected such as to obtain the required volume V of the dose being transferred and to obey the following relationship: $V \approx 1/3 \pi R^3 \cdot 10^{-6}$ nanoliters, where V is the required volume of the droplet forming on the butt rod end after the rod has been withdrawn from the solution, and R in microns is the radius of the butt rod end.

The device as described above is used as follows to facilitate liquid transfer: The base 1 carrying the rods 2 are positioned opposite to the tray 32 in such a manner that each rod is located against a respective well 13 of the tray 32 filled with an aqueous solution 34 of the substance to be transferred, e.g., an aqueous oligonucleotide solution. Then the base 1 is displaced towards the tray 12 until the ends of the rods 2 (FIG. 9 b) contact the solution 34. Then, by displacing the base 1 together with the rods 2, (FIG. 9 c) in the opposite direction, the rods 2 are withdrawn from the solutions, with the result that a microdose 15 (FIG. 9 d) of the solution of the substance is formed on the butt end of each rod 2. The volume V of the microdose is independent of the depth of immersion of the rod 2 into the solution 34 (due to the hydrophilic butt end of the rod and hydrophobic coating on the rod's side surface with respect to the solution being transferred) and is determined substantially by the radius R alone of the butt end of the rod 2.

Figure 10:
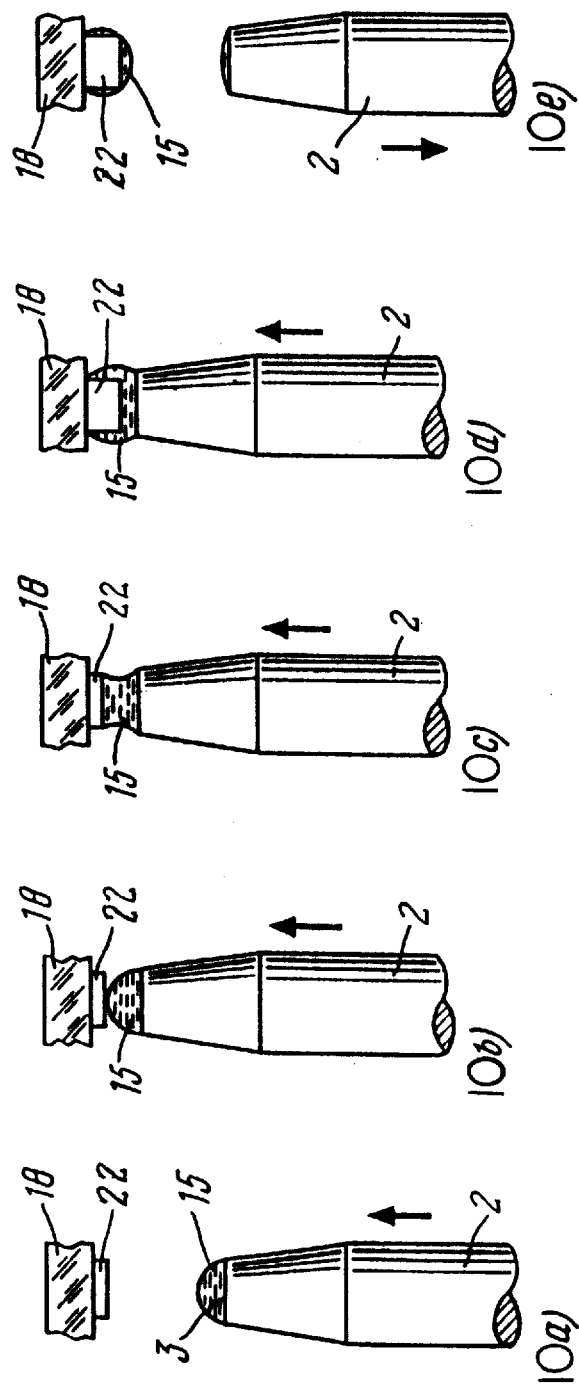
FIGS. 10 A–E is a detailed view of the deposition of aqueous solutions, in accordance with features of the invention.

Next, the base, together with the rods loaded with the microdoses of the solution, is transferred to the gel elements 22 arranged in a micromatrix of the type depicted in FIG. 3. The layout of the gel elements 22 complement the configuration of the oligonucleotide-loaded rods so that when the base 1 is positioned opposite to the surface of the matrix, each rod 2 is opposing a respective gel element 22. Thereupon, the base 1 is displaced towards the matrix 18 along the arrow as depicted in FIG. 10 b, until the microdoses 15 contact the gel areas 22. During transfer, the temperature of the solution 34 and the butt ends 3 are maintained at the dew point of the air to minimize evaporation of the solution during the transfer. Control of the temperature of the butt ends 3 are attained by changing the battery 4 voltage of the thermoelectric cells in response to the signal produced by a temperature transmitter (not shown) in heat contact with the base.

Upon contact with the microdose 15, the gel element 22 vigorously absorbs the solution (FIG. 10 c), with the result that the gel areas 22 swell and the microdoses are drawn into the gel.

After fluid transfer, the base 1 supporting the rods 2 is retracted from the micromatrix. The rods then are washed and dried for reuse.

Oligonucleotide Immobilization Detail

The inventors have developed an immobilization procedure for coupling micromolecules to acrylamide gels so as to minimize liquid evaporation during immobilization and to also ensure that covalent bonding of oligonucleotides to the gel matrix units proceeds to completion. This procedure is more fully disclosed in PCT/RU94/00178, filed on Aug. 11, 1993, to Yershov.

Briefly, the immobilization process is as follows: Microvolumes of bioorganic solutions are loaded onto the micromatrix cells, with the temperature of the micro-matrix being maintained equal to that of the ambient air. Once the micro-volumes of the oligonucleotide solutions have been applied to the cells of the matrix, the micro-matrix temperature is set equal to or below the dew point of the ambient air. This temperature is maintained until swelling of the gel is complete and noncoalescent droplets of water condensate appear in the spacings "B" between the cells.

After the appearance of the water condensate, a thin layer of an inert, nonluminescent oil is applied to the micro-matrix surface so as to prevent oligonucleotide evaporation. An oil layer of at least approximately 100 µm provides good results. A myriad of inert oils are suitable including, but not limited to, purified Vaseline®, phenyl (10 percent) methylsilicone oil, phenyl (20 percent) methylsilicone oil, among others.

The micro-matrix is kept under the oil layer until completion of the oligonucleotide immobilization process, and preferably for 48 hours. The oil is then removed by washing with a polar substance that will not cause oligo denaturing, such as ethanol, or water. The matrix is dried and stored indefinitely, ready for use.

Figure 11:
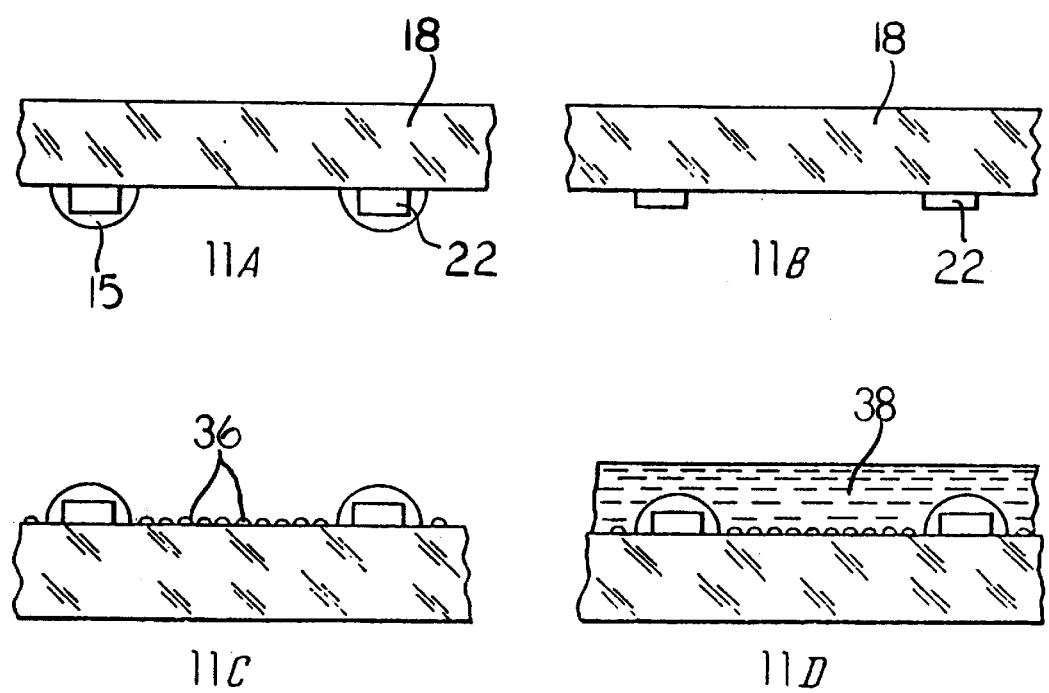
FIGS. 11 A–D is a detailed elevational view of a loaded gel element in progressive stages of development, in accordance with features of the invention.

As disclosed in the above identified PCT application PCT/RU94/00178, the process is illustrated in FIG. 11, wherein a fragment of the micromatrix 18 is shown in a sectional side-elevational view. FIG. 11 a depicts the immobilization sequence at the instant when microvolumes of bioorganic solutions 15 are being loaded to the gel elements 22. At this point, the temperature of the micromatrix 18 is maintained equal to that of the ambient air.

As is depicted in FIG. 11 b, at the completion of loading, all residual droplets of the bioorganic solution 15 evaporate, and the condition of the gel is the same in all cells.

At the instant when the water condensation from the ambient air has been completed, the temperature of the micromatrix 18 is below or equal to the dew point of the ambient air. The gel cells 22 have swollen and are coated with water condensate 36. Minute droplets of condensate also appear in the intercell spacings. As depicted in FIG. 11 c, the droplets do not coalesce with one another.

FIG. 11 d depicts the entire assembly coated with the film 38 of the nonluminescent oil, with a thickness of over 100 microns. The temperature of the micromatrix is equal to that of the ambient air.

This aforementioned process is applicable for immobilizing any water-soluble bioorganic substances to the carrier, especially in cases which require the presence and retention of the liquid (aqueous) phase to facilitate completion of covalent bonding in the system substance-carrier.

Figures 4A, 4B:
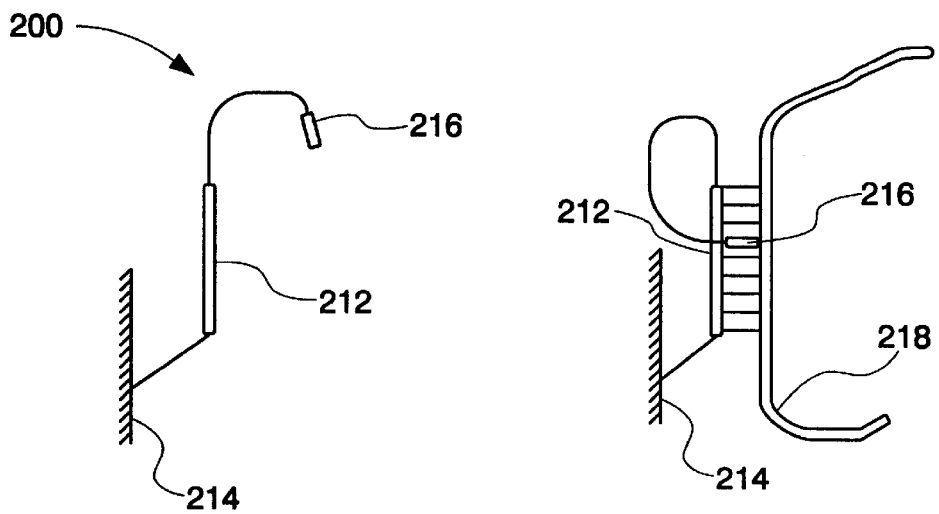
FIGS. 4 A–B is a schematic view of an intercalating compound revealing a duplexed pair of oligonucleotide molecules juxtaposed to a polyacrylamide matrix, in accordance with the present invention.

An exemplary embodiment of the duplex detection method, incorporating the produced micro-matrix topologies, is schematically depicted in FIGS. 4A–B as numeral 200. FIG. 4A depicts an oligomer, 212, immobilized to a gel matrix unit 214. The oligomer is constructed to contain an intercalating tag, 216 such as ethidium bromide. Other intercalating agents, such as propidium iodide, also can be employed.

In the free state, depicted in FIG. 4A, wherein the intercalating agent is not juxtaposed between base planes of a duplex, the tag fluoresces at a certain intensity. Part of this fluorescence is due to higher background and lower-signal-to-background noise that results from intercalating dyes reacting with single-stranded oligonucleotides. However, fluorescence is magnified far above background levels when duplexes do occur. As can be noted in FIG. 4B, when a single strand 218 of a target oligonucleotide molecule, complementary to the immobilized oligomer, is contacted with the loaded gel unit, duplexing occurs. The inventors observed that the intercalating agent, now juxtaposed between the base planes of the duplex, fluoresces at an intensity that is approximately 10 times that observed in the free state. This higher intensity is observed within approximately one minute.

As an alternative to first binding the intercalating agent to the immobilized oligomer, the intercalating agent can instead be bound to the target single strand oligonucleotide molecule 218. In yet another alternative, addition of the intercalating agent can be made after duplexing occurs between the immobilized oligo fraction 212 and the mobilized single strand target sequence 218.

For example, fluorescence enhancements are achieved when intercalating dyes such as thiazole orange homodimer (TOTO) or oxazole yellow homodimer (YOYO) are used, both of which are manufactured by Molecular Probes, Eugene Oreg. DNA binding fluorochromes specific for double-stranded DNA also provide good results.

Use of AT-specific fluorescent ligands that stabilize these pairs also enhance the fluorescent process by equalizing AT stability vis-a-vis GC-rich interactions.

EXAMPLE

Figures 5A, 5B:
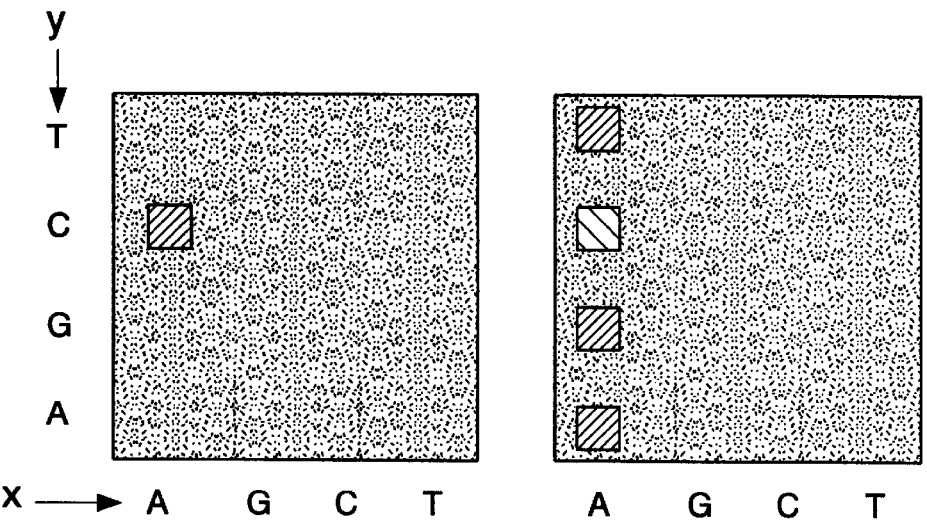
FIGS. 5 A–B is a plan view of a gel matrix disclosing the existence of duplexes when fluorescently labeled oligomer (I) is used, and when intercalating dye (II) is used to detect duplexes, in accordance with the present invention.
Figure 6:
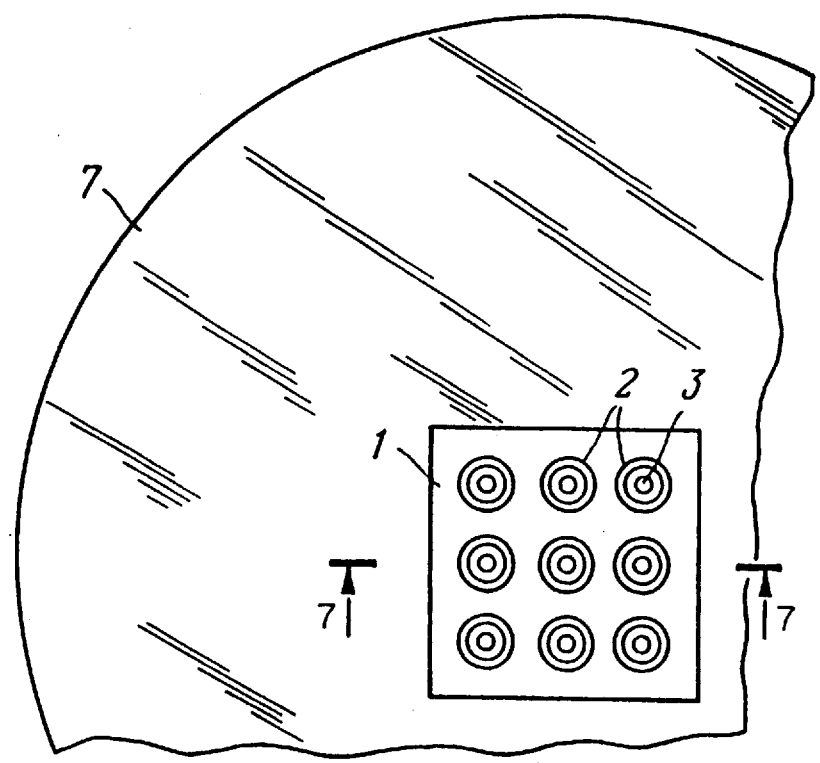
FIG. 6 is a plan view of a device for microdispensing aqueous solutions, in accordance with features of the invention.
Figure 7:
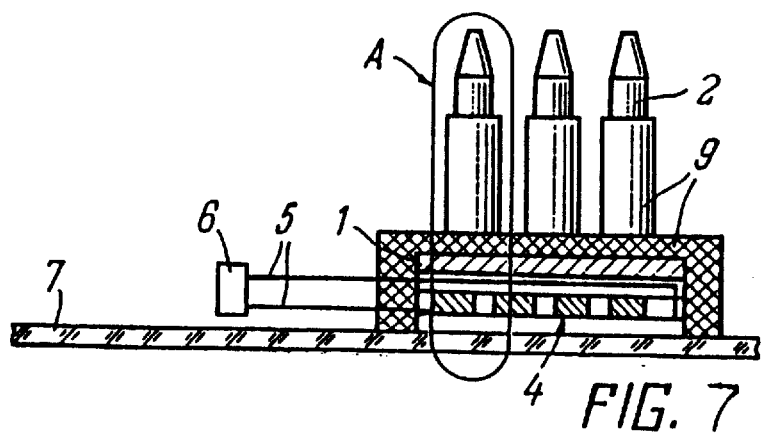
FIG. 7 is an elevational, cross-sectional view of FIG. 6, taken along line 7—7.
Figure 8:
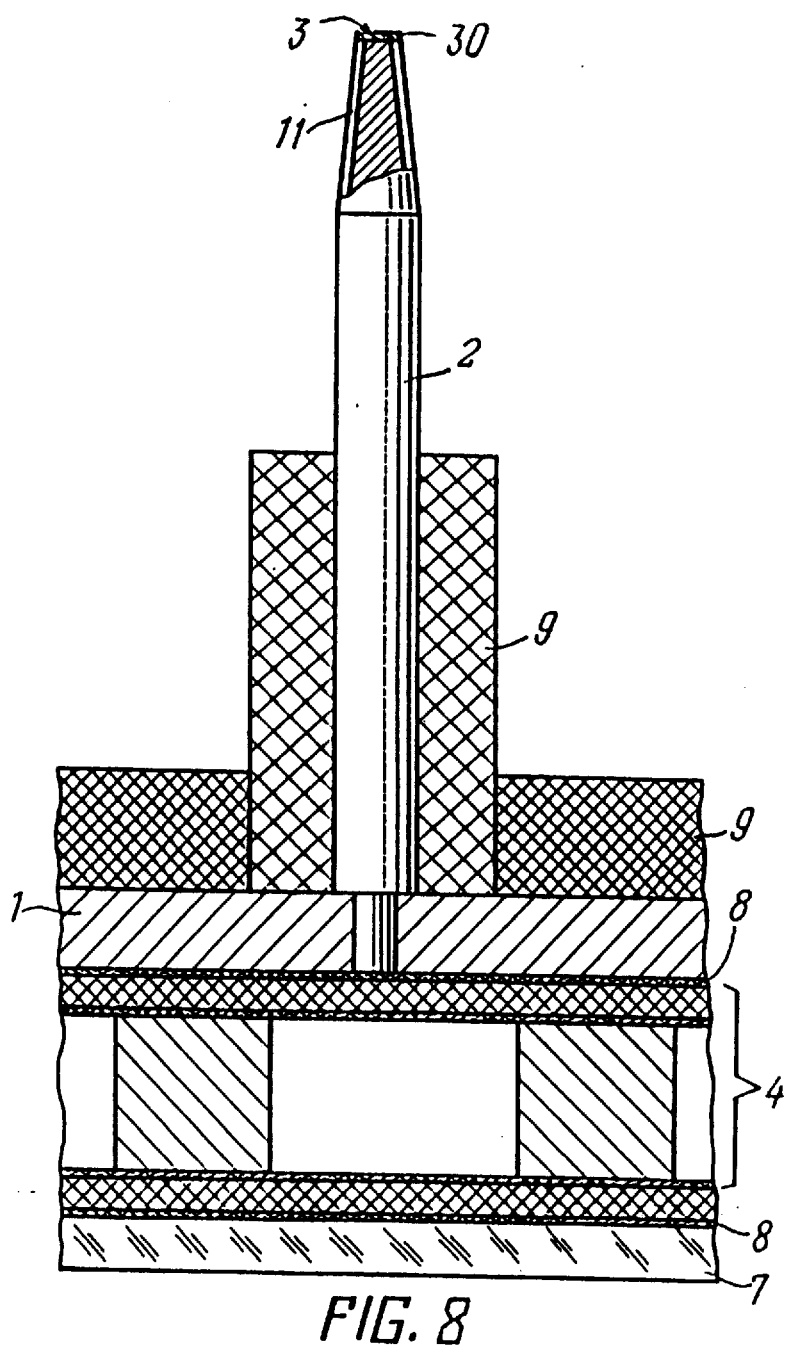
FIG. 8 is an elevational, cross-sectional view of one of the microdispensing probes, in accordance with features of the invention.
Figure 9:
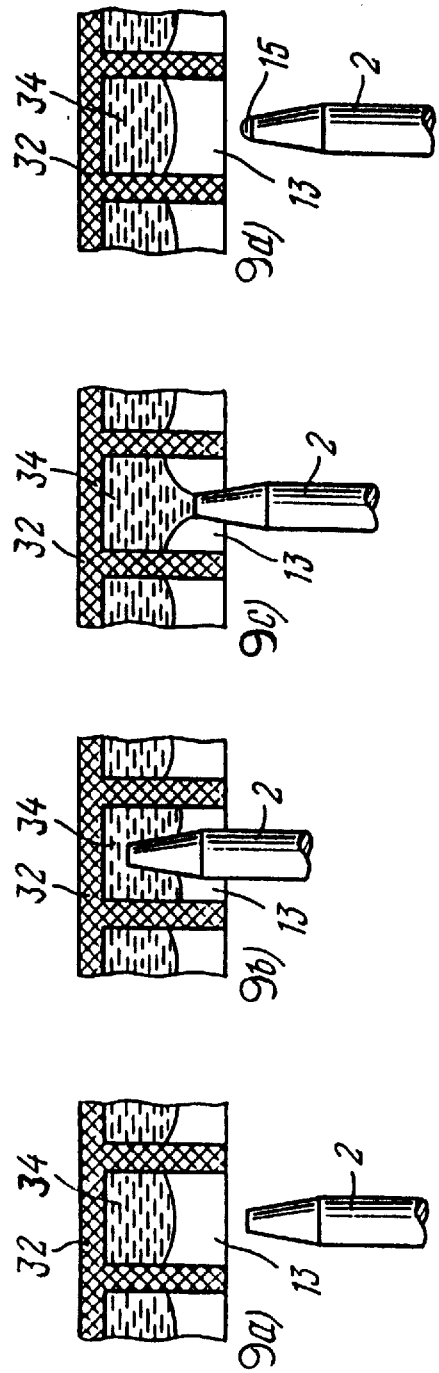
FIGS. 9 A–D is a detailed view of harvesting of aqueous solutions, in accordance with features of the invention.

FIG. 5 illustrates the efficiency of using either fluorescently labeled target ss DNA strings (a) or intercalating dyes (b) to rapidly detect duplex formation. This plan view depicts the same matrix of polyacrylamide cells, whereby the matrix is manufactured by the methods disclosed supra. The matrix is comprised of 16 cells, each cell loaded with the octamer CyAACCxT-5'. As shown, the 3' end is anchored to the gel and not available for further interaction. The immobilized octamer varies at two base positions "y" and "x" as shown along the boundaries of the matrix.

As can be determined in FIG. 5 (A), when the octamer-loaded matrix is hybridized with fluorescently labeled ss DNA, such as the 19-mer CCTGGGCAGGTTGGTATCA, a clear signal is seen when a perfect GC and TA match is made at duplexing. The fluorescent label used in this instance was HEX, available through Applied Biosystems, Foster City, Calif. Another suitable dye is tetramethylrodamine.

In a separate experiment, when the octamer-loaded matrix is hybridized with the unlabeled 19-mer in the presence of an intercalating agent, a clear signal again is seen at the GC and TA matching cell location. This can be noted in FIG. 5 b. Weaker signals also are detected, however. For example, signals were observed when just TA or GC interaction was observed. This indicates that when background noise is controlled, the use of an intercalating agent or a plurality of intercalating agents may be more sensitive than the use of fluorescent dyes for detecting at least partial matches when rapid determinations are desired. The intercalating agent used in this instance, ethidium bromide, was added after the duplexing between oligomer strings occurred.

However, and as discussed supra, intercalating agents also can be first attached to either the shorter oligomer strand prior to immobilization or to the target single strand prior to hybridization.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for determining the existence of duplexes of oligonucleotide complementary molecules comprising:
   a.) constructing a plurality of different oligonucleotide molecules each of a specific length and each having a specific base sequence;
   b.) supplying a matrix having a plurality of cells adapted to receive the oligonucleotide molecules;
   c.) immobilizing the different oligonucleotide molecules in the cells to fill the cells;
   d.) contacting the now-filled cells with single stranded target oligonucleotide molecules to form a duplex;
   e.) contacting the duplex with an intercalating agent; and
   f.) observing fluorescence levels emanating from the intercalating agent without first washing the contacted duplex;

wherein the matrix consists of polyacrylamide.

2. The method as recited in claim 1 wherein the intercalating agent is selected from the group consisting of ethidium bromide, propidium iodide, thiazole orange homodimer, oxazole yellow homodimer, and combinations thereof.

3. The method as recited in claim 1 wherein the fluorescence is observed within 1 minute after duplexing occurs.

4. A method for determining the existence of duplexes of oligonucleotide complementary molecules comprising:
   a.) constructing a plurality of different oligonucleotide molecules each of a specific length and each having a specific base sequence;
   b.) supplying a matrix having a plurality of cells adapted to receive the oligonucleotide molecules;
   c.) immobilizing the different oligonucleotide molecules in the cells to fill the cells;
   d.) contacting the now-filled cells with single stranded target oligonucleotide molecules to form a duplex;
   e.) contacting the duplex with an intercalating agent; and
   f.) observing fluorescence levels emanating from the intercalating agent without first washing the contacted duplex;

wherein the intercalating agent is covalently attached to the immobilized oligonucleotide molecules.

5. A method for determining the existence of duplexes of oligonucleotide complementary molecules comprising:
   a.) constructing a plurality of different oligonucleotide molecules each of a specific length and each having a specific base sequence;
   b.) supplying a matrix having a plurality of cells adapted to receive the oligonucleotide molecules;
   c.) immobilizing the different oligonucleotide molecules in the cells to fill the cells;
   d.) contacting the now-filled cells with single stranded target oligonucleotide molecules to form a duplex;
   e.) contacting the duplex with an intercalating agent; and
   f.) observing fluorescence levels emanating from the intercalating agent without first washing the contacted duplex;

wherein the intercalating agent is covalently attached to the single stranded oligonucleotide molecules.

6. The method as recited in claim 1 wherein the specific length of the different oligonucleotide molecules is selected from a range of between approximately 5 nucleotides and 30 nucleotides.

7. The method as recited in claim 4 wherein fluorescence is analyzed within one minute after duplexing occurs.

8. The method as recited in claim 4 wherein the matrix is comprised of polyacrylamide.

9. The method as recited in claim 5 wherein the fluorescence is analyzed within one minute after duplexing occurs.

10. The method as recited in claim 5 wherein the matrix is comprised of polyacrylamide.

* * * * *